US005710256A

United States Patent [19]

Buechler

[11] Patent Number: 5,710,256
[45] Date of Patent: Jan. 20, 1998

[54] METHADONE DERIVATIVES AND PROTEIN AND POLYPEPTIDE METHADONE DERIVATIVE CONJUGATES AND LABELS

[75] Inventor: Kenneth F. Buechler, San Diego, Calif.

[73] Assignee: Biosite Diagnostics Incorporated, San Diego, Calif.

[21] Appl. No.: 416,034

[22] Filed: Apr. 3, 1995

[51] Int. Cl.[6] .............................. C07K 5/00; C07K 7/00; C07K 17/00; C07K 16/00
[52] U.S. Cl. .............................. 530/388.9; 530/389.8; 530/324; 530/325; 530/326; 530/327; 530/328; 530/329; 530/330; 530/331; 530/387.1; 530/300; 530/350; 562/431; 558/233; 558/250; 558/253; 558/254; 568/21; 568/23; 568/25; 568/27; 568/28; 568/63; 424/1.41; 424/1.45; 424/1.49; 424/1.53
[58] Field of Search ........................ 558/233, 250, 558/253-254; 568/21-23, 25, 27, 28, 63; 549/63; 562/431; 424/1.41, 1.45, 1.49, 1.53; 530/300, 350, 345, 387.1, 324-331, 388.9, 389.8

[56] References Cited

U.S. PATENT DOCUMENTS

| | | |
|---|---|---|
| 3,843,696 | 10/1974 | Wagner et al. . |
| 3,966,556 | 6/1976 | Rubenstein et al. . |
| 4,067,774 | 1/1978 | Rubenstein et al. . |
| 4,104,367 | 8/1978 | Gomez et al. . |
| 4,952,336 | 8/1990 | Brynes et al. . |
| 5,028,535 | 7/1991 | Buechler et al. . |
| 5,089,391 | 2/1992 | Buechler et al. ............ 435/7.1 |
| 5,237,057 | 8/1993 | Buechler et al. ............ 536/119 |

FOREIGN PATENT DOCUMENTS

| | | |
|---|---|---|
| 0380019 | 1/1990 | European Pat. Off. . |
| 9320067 | 10/1993 | WIPO . |
| 9411405 | 5/1994 | WIPO . |

OTHER PUBLICATIONS

De Cato et al., "Immunologic Studies on Drug Addiction: II. Specificity and Application of Antibodies Reactive with Methadone," *Clinical Immunology and Immunopathology* 9:293–300 (1978).

Brode and Hill, "The Optical Resolution of Amidone," *JOC* 13:191–102 (1948).

Cummins and Cummins, "Cardiac Specific Troponin–I Release in Canine Experimental Myocardial Infarction: Development of a Sensitive Enzyme–Linked Immunoasay," *J. Mol. Cell. Cardiol.* 19:999–1010 (1987).

Cummins et al., "Cardiac Specific Troponin–I Radioimmunoassay in the Diagnosis of Acute Myocardial Infarction," *American Heart Journal* 113:1333–1344 (1987).

Cummins et al., "Comparison of Serum Cardiac Specific Troponin–I with Creatine Kinase, Creatine Kinase–MB Isoenzyme, Tropomyosin, Myoglobin and C–Reactive Protein Release in Marathon Runners: Cardiac or Skeletal Muscle Trauma?" *European Journal of Clinical Investigation* 17:317–324 (1987).

Easton et al., "A New Synthesis and Confirmation of the Structure of Amidone," *JACS* 69:2941–2943 (1947).

Easton et al., "The Structure of Isoamidonek. I," 74:5772 (1952).

Eddy et al., "Chemistry and Pharmacology of the Methadols and Acetylmethadols," *JOC* 17:321–326 (1952).

Katagiri et al., "Alterations in Cardiac Troponin Subunits in Myocardial Infarction," *Japan Heart J.* 22:653–664 (1981).

Katagiri, T., "Changes of Cardiac Structural Proteins in Myocardial Infarction," *Japan Heart J.* 18:711–721 (1977).

Pohland et al., "Optically Active Compounds Related to Methadon," *JACS* 71:460–462 (1949).

Pohland et al., "Synthesis and Identification of Metabolites Resulting from the Biotransformation of DL–Methadone in Man and in the Rat," *J. Med. Chem.* 14:194–197 (1971).

Schultz et al., "The Reaction of 1–Dimethylamino–2–chloropropane with Diphenylacteonitrile. The Structure of Amidone," *JACS* 69:2454–2459 (1947).

Speeter et al., "Analgesic Carbinols and Esters Related to Amidone (Methadon)," *JACS* 71:57–60 (1949).

Toyo–Oka and Ross, "$Ca^{2+}$ Senstivity Change and Troponin Loss in Cardiac Natural Actomyosin After Coronary Occlusion," *Amer. J. of Phys.*, vol. 240, No. 5:H704–H708 (1981).

*Primary Examiner*—Toni R. Scheiner
*Assistant Examiner*—Sheela J. Huff
*Attorney, Agent, or Firm*—Lyon & Lyon LLP

[57] ABSTRACT

The present invention is directed to novel methadone derivatives which are synthesized for the covalent attachment to antigens (proteins or polypeptides) for the preparation of antibodies or receptors to methadone and methadone metabolites. The resulting novel antigens may be used for the production of antibodies or receptors using standard methods. Once generated, the antibodies or receptors and the novel derivatives which are covalently attached to proteins, polypeptides or labels may be used in the immunoassay process.

6 Claims, 6 Drawing Sheets

METHADONE DERIVATIVES AND PROTEIN AND POLYPEPTIDE METHADONE DERIVATIVE CONJUGATES AND LABELS

FIELD OF THE INVENTION

This invention is in the field of ligand receptor assays, including immunoassays, for the detection of methadone and selected metabolites of methadone in a fluid sample. More particularly, this invention relates to methods for the synthesis of novel methadone derivatives and protein and polypeptide methadone derivative conjugates and labels for use in the preparation of antibodies to methadone metabolites and for use in the immunoassay process.

BACKGROUND OF THE INVENTION

Methadone was first used as a substitute for morphine because it possesses many of the pharmacological properties of morphine. Methadone is also nearly as potent an analgesic as morphine but the clinical use of methadone has been for the treatment of opiate addicts. The monitoring of patients on methadone maintenance has resulted in a medical need for antibodies and diagnostics to rapidly detect methadone and methadone metabolites in order to monitor and treat opiate addiction.

The preparation of antibodies to methadone and methadone metabolites requires the synthesis of methadone derivatives in order to covalently attach the derivative to an antigenic polypeptide or protein. In addition, the methadone derivative is covalently attached to various polypeptides, proteins or labels for use in screening antibodies and in the immunoassay process. The methadone derivative should mimic the structure of the methadone metabolites sought to be measured. Therefore, the selection and synthesis of the types of methadone derivatives for covalent attachment to proteins, polypeptides or labels is critical. In addition, the methadone derivatives need to be stable and soluble in an aqueous solution.

Methadone compounds and conjugates for immunization and immunoassay have been described in U.S. Pat. Nos. 3,843,696, 3,966,556, 4,104,367 and a European Patent Application No. 380019.

SUMMARY OF THE INVENTION

The present invention is directed to novel methadone derivatives which are synthesized for the covalent attachment to antigens (proteins or polypeptides) for the preparation of antibodies to methadone and the methadone metabolites. The resulting novel antigens may be used for the production of antibodies using standard methods. Once generated, the antibodies and the novel derivatives which are covalently attached to proteins, polypeptides or labels may be used in the immunoassay process.

Definitions

In accordance with the present invention and as used herein, the following terms, are defined with the following meanings, unless explicitly stated otherwise.

"Drug" shall mean any compound or ligand which either as a result of spontaneous chemical reaction or by enzyme catalyzed or metabolic reaction, generates an intrinsic activity when administered to a biological system. The drug may be metabolized to a derivative of the drug by a biological system. Common examples of drugs and their metabolites are methadone, morphine, barbiturates, tetrahydrocannabinol, phencyclidine, amphetamines, methamphetamines, opiates, benzodiazepines, cocaine, estrone-3-glucuronide, pregnanediol-glucuronide, cotinine, lysergic acid diethylamide, propoxyphene, anabolic steroids, tricyclic anti-depressants.

"Drug derivative" shall mean a ligand derivative, drug, drug metabolite or a drug analogue conjugated to a linking group.

"Drug metabolite" shall mean a compound upstream or downstream from a drug in a biochemical or metabolic pathway, or an intermediate.

"Label" shall mean a signal development element or a means capable of generating a signal, for example, a dye or an enzyme. The attachment of a drug derivative to the label can be through covalent bonds, adsorption processes, hydrophobic and/or electrostatic bonds, as in chelates and the like, or combinations of these bonds and interactions.

"Binding domain" shall refer to the molecular structure associated with that portion of a receptor that binds ligand. More particularly, the binding domain may refer to a polypeptide, natural or synthetic, or nucleic acid encoding such a polypeptide, whose amino acid sequence represents a specific region of a protein, said domain, either alone or in combination with other domains, exhibiting binding characteristics which are the same or similar to those of a desired ligand/receptor binding pair. Neither the specific sequences nor the specific boundaries of such domains are critical, so long as binding activity is exhibited. Likewise, used in this context, binding characteristics necessarily includes a range of affinities, avidities and specificities, and combinations thereof, so long as binding activity is exhibited.

"Linking group" shall mean the "chemical arm" between the protein, polypeptide or label and a drug or drug derivative. As one skilled in the art will recognize, to accomplish the requisite chemical structure, each of the reactants must contain the necessary reactive groups. Representative combinations of such groups are amino with carboxyl to form amide linkages, or carboxy with hydroxy to form ester linkages or amino with alkyl halides to form alkylamino linkages, or thiols with thiols to form disulfides, or thiols with maleimides or alkylhalides to form thioethers. Obviously, hydroxyl, carboxyl, amino and other functionalities, where not present may be introduced by known methods. Likewise, as those skilled in the art will recognize, a wide variety of linking groups may be employed. The structure of the linkage should be a stable covalent linkage formed to attach the drug or drug derivative to the protein, polypeptide or label. In some cases the linking group may be designed to be either hydrophilic or hydrophobic in order to enhance the desired binding characteristics of the ligand and the receptor. The covalent linkages should be stable relative to the solution conditions under which the ligand and linking group are subjected. Generally preferred linking groups will be from 1–20 carbons and 0–10 heteroatoms (NH, O, S) and may be branched or straight chain. Without limiting the foregoing, it should be obvious to one skilled in the art that only combinations of atoms which are chemically compatible comprise the linking group. For example, amide, ester, thioether, thioester, keto, hydroxyl, carboxyl, ether groups in combinations with carbon-carbon bonds are acceptable examples of chemically compatible linking groups. Other chemically compatible compounds which may comprise the linking group are set forth in this Definition section and hereby are incorporated by reference.

"Hydrocarbyl" shall refer to an organic radical comprised of carbon chains to which hydrogen and other elements are attached. The term includes alkyl, alkenyl, alkynyl and aryl groups, groups which have a mixture of saturated and unsaturated bonds, carbocyclic rings and includes combinations of such groups. It may refer to straight-chain, branched-chain cyclic structures or combinations thereof.

"Aryl" shall refer to aromatic groups which have at least one ring having a conjugated pi electron system and includes carbocyclic aryl, heterocyclic aryl and biaryl groups, all of which may be optionally substituted.

"Carbocyclic aryl groups" shall refer to groups wherein the ring atoms on the aromatic ring are carbon atoms. Carbocyclic aryl groups include monocyclic carbocyclic aryl groups and optionally substituted naphthyl groups.

"Monocyclic carbocyclic aryl" shall refer to optionally substituted phenyl, being preferably phenyl or phenyl substituted by one to three substituents, such being advantageously lower alkyl, hydroxy, lower alkoxy, lower alkanoyloxy, halogen, cyano, trihalomethyl, lower acylamino, lower amino or lower alkoxycarbonyl.

"Optionally substituted naphthyl" shall refer to 1- or 2-naphthyl or 1- or 2-naphthyl preferably substituted by lower alkyl, lower alkoxy or halogen.

"Heterocyclic aryl groups" shall refer to groups having from 1 to 3 heteroatoms as ring atoms in the aromatic ring and the remainder of the ring atoms carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl, and the like, all optionally substituted.

"Optionally substituted furanyl" shall refer to 2- or 3-furanyl or 2- or 3-furanyl preferably substituted by lower alkyl or halogen.

"Optionally substituted pyridyl" shall refer to 2-, 3- or 4-pyridyl or 2-, 3- or 4-pyridyl preferably substituted by lower alkyl or halogen.

"Optionally substituted thienyl" shall refer to 2- or 3-thienyl, or 2- or 3-thienyl preferably substituted by lower alkyl or halogen.

"Biaryl" shall refer to phenyl substituted by carbocyclic aryl or heterocyclic aryl as defined herein, ortho, meta or para to the point of attachment of the phenyl ring, advantageously para; biaryl is also represented as the —C$_6$H$_4$—Ar substituent where Ar is aryl.

"Aralkyl" shall refer to an alkyl group substituted with an aryl group. Suitable aralkyl groups include benzyl, picolyl, and the like, and may be optionally substituted.

"Lower" referred to herein in connection with organic radicals or compounds respectively defines such with up to and including 7, preferably up to and including 4 and advantageously one or two carbon atoms. Such groups may be straight chain or branched.

The terms (a) "alkyl amino," (b) "arylamino," and (c) "aralkylamino," respectively, shall refer to the groups —NRR' wherein respectively, (a) R is alkyl and R' is hydrogen or alkyl; (b) R is aryl and R' is hydrogen or aryl, and (c) R is aralkyl and R' is hydrogen or aralkyl.

The term "acyl" shall refer to hydrocarbyl—CO— or HCO—.

The terms "acylamino" refers to (RCONCR)— and (RCO$_2$N)— respectively, wherein each R is independently hydrogen or hydrocarbyl.

The term "hydrocarbyloxycarbonylmethyl" shall refer to the group ROC(O)O— wherein R is hydrocarbyl.

The term "lower carboalkoxymethyl" or "lower hydrocarbyloxycarbonylmethyl" refers to hydrocarbyl—OC(O) CH$_2$— with the hydrocarbyl group containing ten or less carbon atoms.

The term "carbonyl" refers to —C(O)—.

The term "carboxamide" or "carboxamido" refers to —CONR$_2$ wherein each R is independently hydrogen or hydrocarbyl.

The term "lower hydrocarbyl" refers to any hydrocarbyl group of ten or less carbon atoms.

The term "alkyl" refers to saturated aliphatic groups including straight-chain, branched chain and cyclic groups.

The term "alkenyl" refers to unsaturated hydrocarbyl groups which contain at least one carbon-carbon double bond and includes straight-chain, branched-chain and cyclic groups.

The term "alkynyl" refers to unsaturated hydrocarbyl groups which contain at least one carbon-carbon triple bond and includes straight-chain, branched-chain and cyclic groups.

The term "hydrocarbyloxycarbonylamino" refers to a urethane, hydrocarbyl—O—CONR— wherein R is H or hydrocarbyl and wherein each hydrocarbyl is independently selected.

The term "di(hydrocarbyloxycarbonyl)amino" refers to (hydrocarbyl—O—CO)$_2$N— wherein each hydrocarbyl is independently selected.

The term "hydrocarbylamino" refers to —NRR' wherein R is hydrocarbyl and R' is independently selected hydrocarbyl or hydrogen.

The term "mercapto" refers to SH or a tautomeric form.

The term "methine" refers to

The term "methylene" refers to —CH$_2$—.

The term "alkylene" refers to a divalent straight chain or branched chain saturated aliphatic radical.

The term "oxy" refers to —O— (oxygen).

The term "thio" refers to —S— (sulfur).

"Disulfide" refers to —S—S—.

"Thioester" refers to

"Thioether" refers to C—S—C.

"Ester" refers to

"Analyte" shall mean substance of natural or synthetic origin sought to be detected and/or measured, said substance having a specific binding partner capable of a specific interaction with said analyte.

"Ligand" shall mean a binding partner to a ligand receptor. A substance which, if detected may be used to infer the presence of an analyte in a sample, including, without limitation, haptens, hormones, antigens, antibodies, deoxyribonucleic acid (DNA), ribonucleic acid (RNA), metabolites of the aforementioned materials and other substances of either natural or synthetic origin which may be of diagnostic interest and have a specific binding partner therefor, i.e., the ligand receptor of a ligand-receptor assay.

"Receptor" shall mean a receptor capable of binding ligand, typically an antibody, or a fragment thereof, but which may be another ligand, depending on assay design.

"Ligand-Receptor Assay" shall mean an assay for an analyte which may be detected by the formation of a complex between a ligand and a ligand receptor which is capable of a specific interaction with that ligand. Ligand-Receptor assays may be competitive or non-competitive, homogeneous or heterogeneous.

"Immunogen" shall mean a chemical or biochemical structure, determinant, antigen or portion thereof, which elicits an immune response, including, for example, polylysine, bovine serum albumin and keyhole limpid hemocyanin (KLH).

"Antigenic" shall mean a chemical or biochemical structure, determinant, antigen or portion thereof which is capable of inducing the formation of an antibody.

DETAILED DESCRIPTION OF THE PREFERRED EMBODIMENTS

Figure 1:
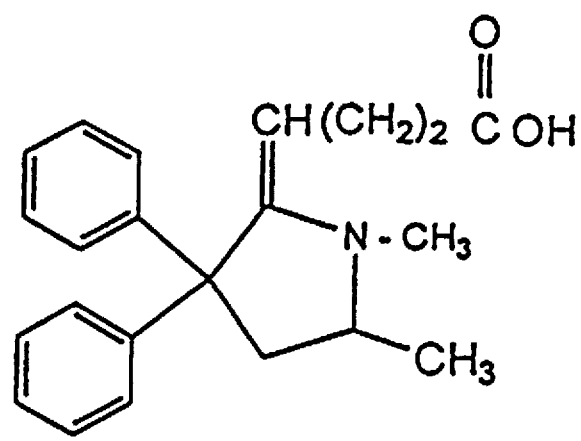
FIGS. 1–4 depict the structures of compounds of this invention.

Novel compounds are described which are used in the generation of antibodies and in the immunoassay process generally. The compounds are derivatives of methadone and the methadone metabolites. The elaboration of methadone can be performed at either end of the methadone molecule; that is, the ethyl keto group may be substituted with another aliphatic keto group which includes an amine, carboxylic acid or thiol function to aid in the attachment of the derivative to the protein, polypeptide or label. In addition, the opposite end of the methadone molecule can be elaborated, for example, starting with normethadone and alkylating the secondary amine with a haloalkyl thioester or acylating with a carboxylic acid thioester. The elaboration of methadone metabolites, for example, 2-ethylidene-1,5-dimethyl-3,3-diphenylpyrrolidine (EDDP) and 2-ethyl-5-methyl-3,3-diphenylpyrroline (EMDP) can be performed on the pyrrolidine or the pyrroline rings, respectively. The synthesis of a particular derivative should allow for the character of the methadone or methadone metabolite derivative to be properly presented to the antibody or receptor in a manner which allows for the desired binding interaction. The synthesis of the linking group between the protein, polypeptide or label and the methadone or methadone metabolite derivative is designed to achieve the desired binding of the drug derivative and the receptor. For example, the derivative may be displaced from the surface of the protein, polypeptide or label to allow the derivative to present itself to the binding domain of receptors.

In general, the compounds of this invention have the following formula:

where R is a linking group comprising one of the following:

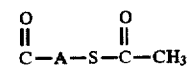

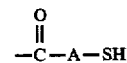

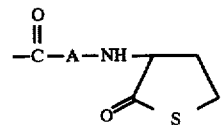

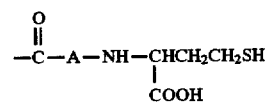

where A is a linking group of from 1 to 20 carbons and from 0 to 10 heteroatoms (H, O, S), either branched or straight chain.

In addition, the general form of the immunogenic protein or polypeptide molecule or the protein or polypeptide molecule or label which is derivatized via an amide, disulfide, thioether, or ester bond to the molecule or label also to a compound of the formula, is of the following:

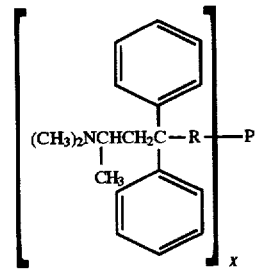

where P is an antigenic protein or polypeptide or a protein, polypeptide or label;

where x is at least one and not greater than 100;

where R is a linking group comprising one of the following:

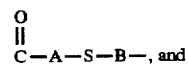

-continued

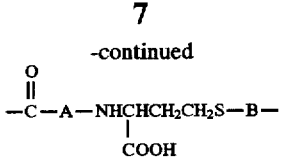

where A is a linking group of from 1 to 20 carbons and 0 to 10 heteroatoms (HN, O, S) either branched or straight chain;

where B is a linking group ultimately attached to a protein, polypeptide or label selected from the group comprising:

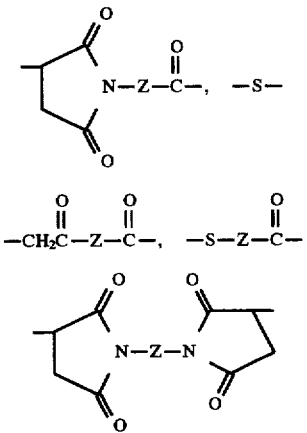

where Z is a linking group of from 1 to 20 carbons and 0 to 10 heteroatoms (NH, O, S) and may be branched or straight chain.

In general, the compounds of this invention also have the following formula:

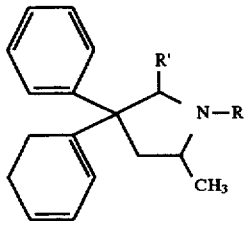

where R' is a saturated or unsaturated aliphatic group of between 0 and 5 carbon atoms; (or hydrogen when R' is O).

where R is a linking group comprising one of the following:

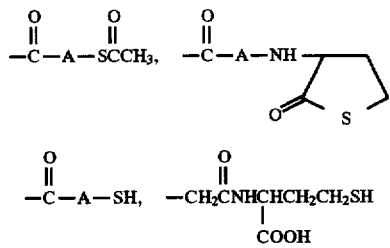

where A is a linking group of from 1 to 20 carbons and from 0 to 10 heteroatoms (NH, O, S), either branched or straight chain.

In addition, the general form of the immunogenic protein or polypeptide molecule or the protein or polypeptide molecule or label which is derivatized via an amide, disulfide, thioether, or ester bond to the molecule or label also to a compound of the formula, is of the following:

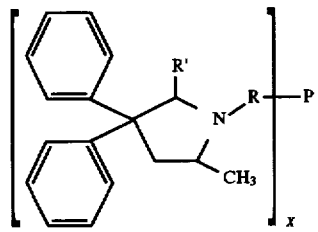

where P is an antigenic protein or polypeptide or a protein, polypeptide or label;

where x is at least one and not greater than 100;

where R' is a saturated or unsaturated aliphatic group of between 0 and 5 carbon atoms.

where R is a linking group comprising one of the following:

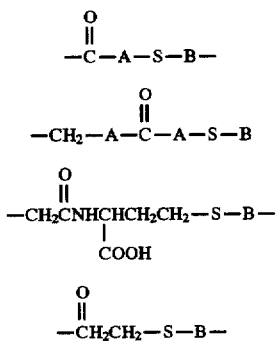

where A is a linking group of from 1 to 20 carbons and 0 to 10 heteroatoms (NH, O, S), either branched or straight chain;

where B is a linking group ultimately attached to a protein, polypeptide or label selected from the group consisting of:

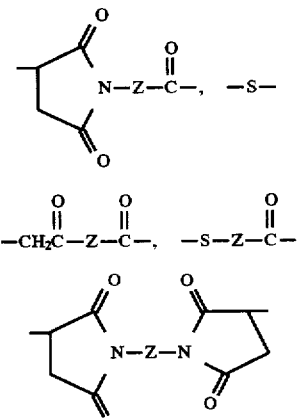

where Z is a linking group of from 1 to 20 carbons and 0 to 10 heterocarbons (NH, O, S) and may be branched or straight chain.

In general, the compounds of this invention also have the following formula:

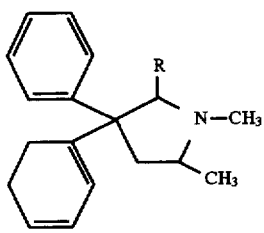

where R is a saturated or unsaturated linking group comprising one of the following:

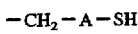
—CH$_2$—A—SH

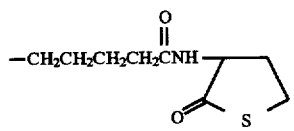

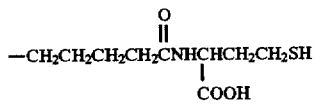

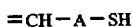
=CH—A—SH

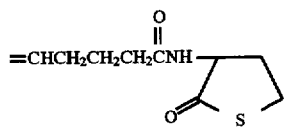

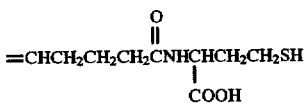

where A is a linking group of from 1 to 20 carbons and from 0 to 10 heterocarbons (NH, O, S), either branched or straight chain.

In addition, the general form of the immunogenic protein or polypeptide molecule or the protein or polypeptide molecule or label which is derivative via an amide, disulfide, thioether, or ester bond to the molecule or label also to a compound of the formula is of the following:

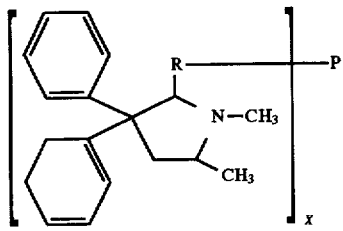

Where P is an antigenic protein or polypeptide or a protein, polypeptide or label;

Where x is at least one and not greater than 100;

Where R is a linking group comprising one of the following:

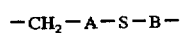
—CH$_2$—A—S—B—

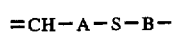
=CH—A—S—B—

-continued

—CH$_2$CH$_2$CH$_2$CH$_2$CNHCHCH$_2$CH$_2$—S—B—
                        |
                       COOH

Where A is a linking group of from 1 to 20 carbons and 0 to 10 heterocarbons (NH, O, S), either branched or straight chain;

Where B is a linking group ultimately attached to a protein, polypeptide, or label selected from the group comprising:

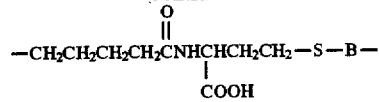

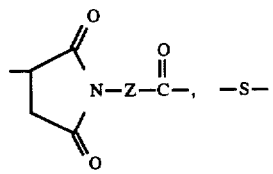

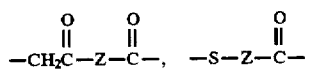

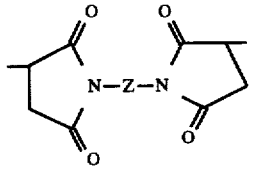

where Z is a linking group of from 1 to 20 carbons and 0 to 10 heterocarbons (NH, O, S) and may be branched or straight chain.

In general, the compounds of this invention also have the following formula:

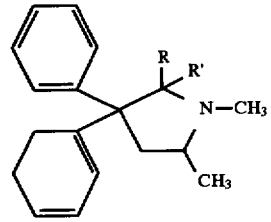

Where R' is —CH$_3$ or —CH2CH$_3$.

Where R is a saturated or unsaturated linking group comprising one of the following:

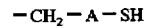
—CH$_2$—A—SH

—CH$_2$NHCH$_2$—A—SH

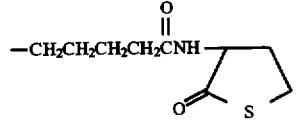

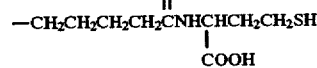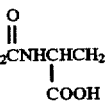

-continued

—CH₂NHCCH₂CH₂SCCH₃ (with two C=O groups)

—CH₂NHCH₂CCH₂CH₂SH (with C=O)

In addition, an immunogenic protein or polypeptide molecule or the protein or polypeptide molecule or label which is derivatized via an amide or ester bond to the molecule or label to a compound of the formula, is of the following:

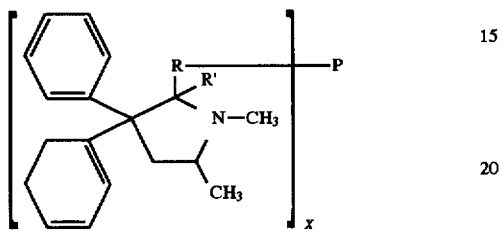

where P is an antigenic protein or polypeptide or a protein, polypeptide or label;

where x is at least one and not greater than 100;

Where R' is —CH₃ or —CH₂CH₃

Where R is a linking group comprising of one of the following:

—CH₂NHCA—S—B—

—CH₂NHCCH₂CH₂S—B—

—CH₂NHCH₂—A—S—B—

—CH₂NHCH₂CNHCHCH₂CH₂S—B
　　　　　　　　|
　　　　　　　COOH

Where A is the linking group of 1 to 20 carbons and 0 to 10 heterocarbons (NH, O, S), either branched or straight chain;

Where B is a linking group ultimately attached to a protein, polypeptide or label selected from the group comprising:

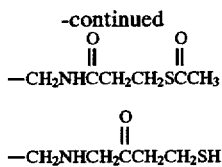

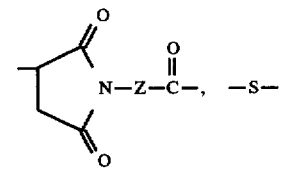

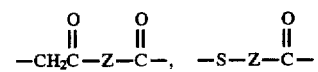

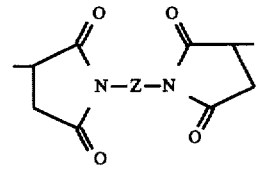

where Z is a linking group of from 1 to 20 carbons and 0 to 10 heterocarbons (NH, O, S) and may be branched or straight chain.

The preferred (best mode) compounds of this invention have the following formula:

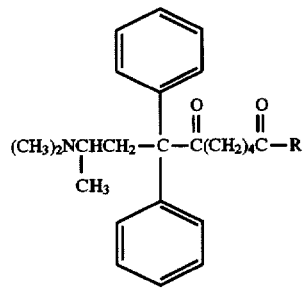

Where R is a linking group comprising one of the following:

—NHCHCH₂CH₂SH
　|
　COOH

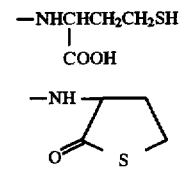

In addition, the preferred (best mode) immunogenic protein or polypeptide molecule or the protein or polypeptide molecule or label derivatized via an amide or ester bond to the molecule or label to a compound of the formula is of the following:

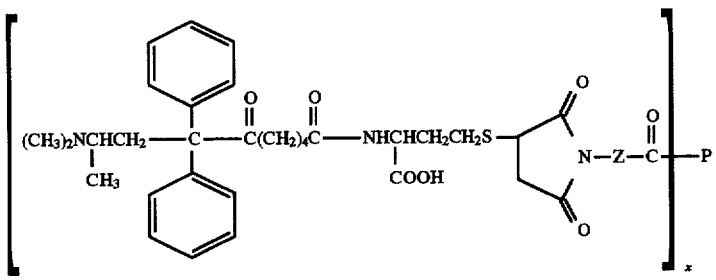

where P is an antigenic protein or polypeptide or a protein, polypeptide or label;

where x is at least one and not greater than 100;

Where Z is a linking group of from 1 to 20 carbons and 0 to 10 heterocarbons (NH, O, S) and may be branched or straight chain.

Of particular interest are methadone derivatives which have been synthesized by substitution of the ethyl keto group of methadone with a linking group containing a thioester function. Methadone derivatives can also be synthesized by alkylation or acylation of the secondary amine of a precursor of normethadone. The alkylation reactions can be performed using various chain length alkyl halide carboxylic acids, for example, 3-iodopropionic acid or ethyl-3-iodo propionate can be reacted to form an N-alkylated carboxylic acid methadone derivative, which can then be further reacted with an amino alkyl thiol ester, such as homocysteine thiolactone, to synthesize the thiol ester derivative of methadone. Acylation reactions can also be performed with normethadone and various chain length alkyl thioester carboxylic acids, for example, 3-acetylthio propionic acid, to synthesize an amide thio ester derivative of methadone.

Figure 2:
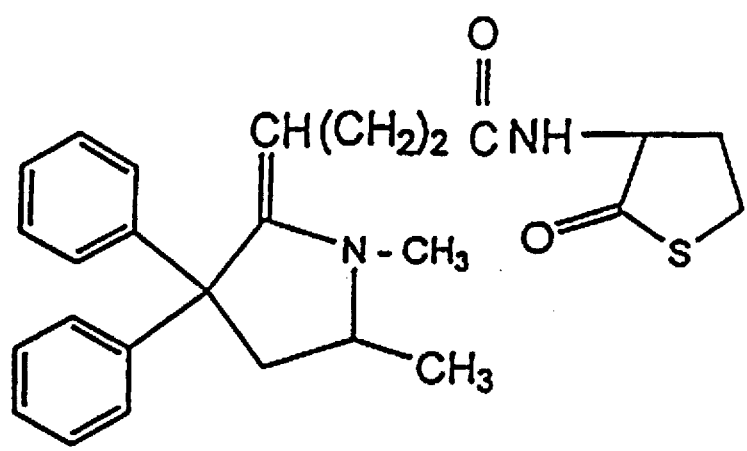

The attachment of linking arms to methadone metabolites, for example, the EDDP and the EMDP, can be performed through derivatization of the pyrrolidine and pyrroline rings, respectively. In the case of the synthesis of thiol ester derivatives of the EDDP molecule, for example, elaboration of the ethyl keto function of methadone to an alkyl carboxylic acid (example 2), or alkyl thio ester (example 3) is first performed and then the methadone thio ester derivative is converted into the normethadone thio ester derivative so that a Schiff base of the secondary amine and the keto function can form. Further isomerization of the Schiff base to the unsaturated alkyl substitutent, mimicking the EDDP structure, then forms the 2ethylenealkyl carboxylic acid derivative of EDDP (FIG. 1) or the 2-ethylenealkyl thio ester derivative of EDDP (FIG. 2), respectively. The ethylene carboxylic acid derivative of EDDP (FIG. 1) can be further reacted with an amino alkyl thioester, such as homocysteine thiolactone to form the thio ester derivative of EDDP (FIG. 2).

Figure 3:
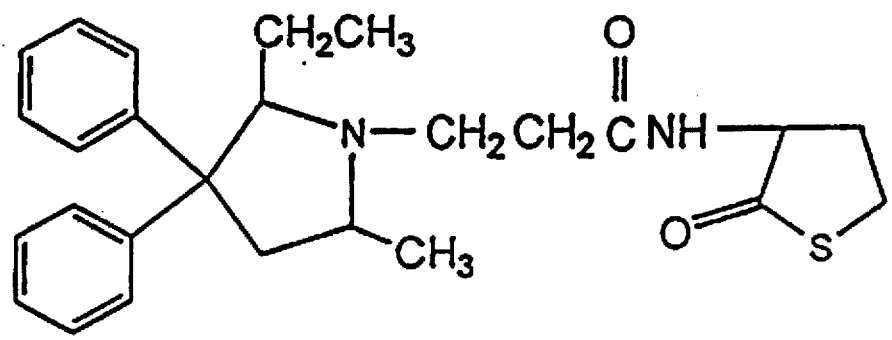
Figure 4:
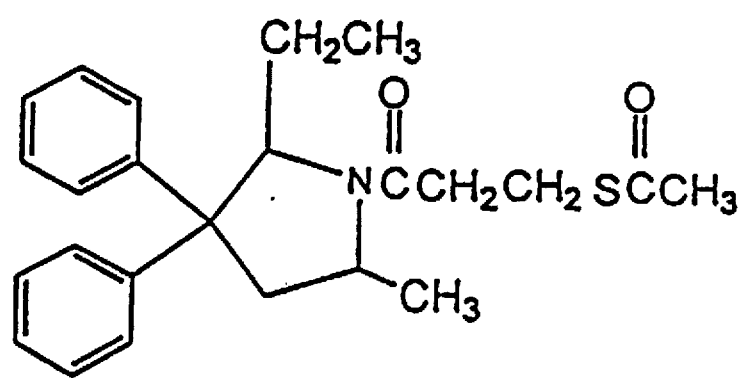
Figure 5:
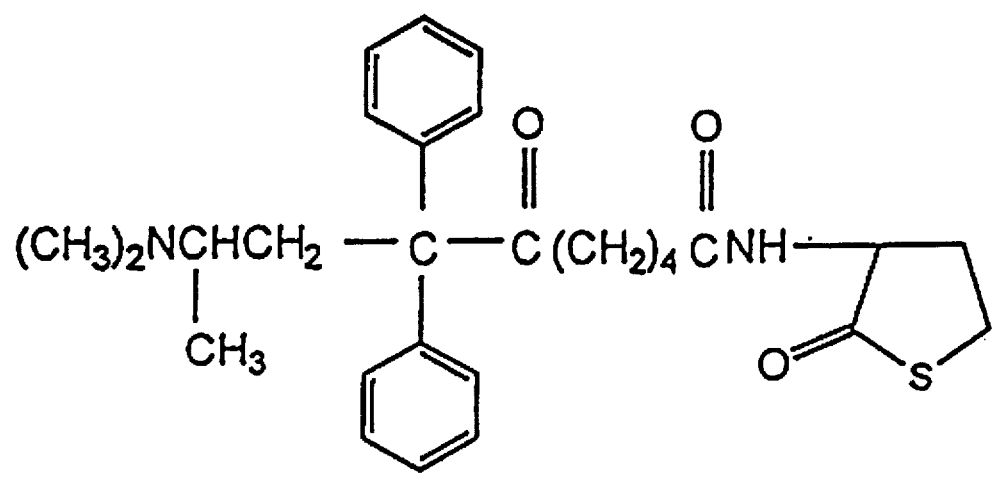
FIGS. 5 and 6 depict the structures of Examples 3 and 4, respectively.
Figure 6:
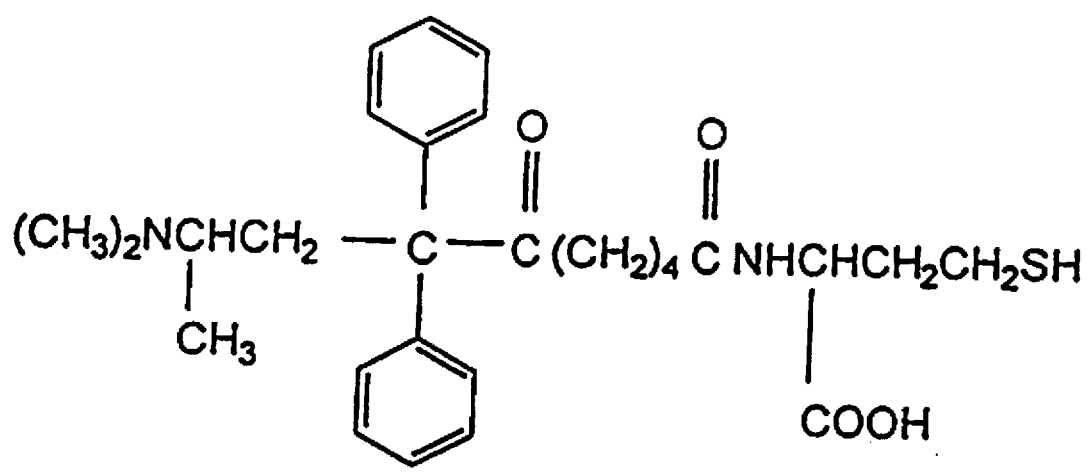

In another aspect of the instant invention, the synthesis of thio ester derivatives of EMDP can be accomplished. The Schiff base of the EMDP is reduced with, for example, sodium cyanoborohydride, and the resulting secondary amine of the EMDP derivative may be either alkylated with various chain length alkyl halide carboxylic acids, for example, 3-iodopropionic acid, to form the N-alkylated carboxylic acid of EMDP derivative, which can be further reacted with an amino alkyl thio ester, such as homocysteine thiolactone, to synthesize the thio ester derivative of EMDP (FIG. 3), or acylated with various chain lengths of carboxylic acid alkyl thio esters, such as 3-acetylthiopropionic acid to form the thio ester derivative of EMDP (FIG. 4).

The thio esters of the resulting methadone or methadone metabolite derivatives are hydrolyzed in dilute base, for example, 0.01M potassium hydroxide, to generate the thiol group which is reacted with the thiol reactive group, such as a maleimide, an alkyl halide or a thiol. Those skilled in the art can recognize the versatility of synthetic strategies described herein.

The compounds are synthesized as thiols or thiol esters so that their covalent attachment to proteins, polypeptides or labels can easily be performed under mild conditions, for example, pH 7 in a protein solution. The protein, polypeptide or label is reacted with a reagent which incorporates a maleimide or an alkylhalide or a thiol into the molecule. These reagents and methods for their use are available from Pierce, Rockford, Ill., for example, for incorporation of maleimide groups onto proteins, polypeptides or labels one can use succinimidyl 4-(N-maleimidomethyl)cyclohexane-1-carboxylate (SMCC), succinimidyl 4-(p-maleimidophenyl)butyrate (SMPB) or m-maleimidobenzoyl-N-hydroxysuccinimide ester (MBS). For introduction of an alkyl halide into a protein, polypeptide or label one can use N-succinimidyl(4-iodoacetyl) aminobenzoate (SIAB) also from Pierce. For introduction of a thiol group into a protein, polypeptide or label, one can use N-Succinimidyl 3-(2-pyridyldithio)propionate (SPDP) also from Pierce. The thiol reactive group, such as maleimide, an alkyl halide or a thiol can be incorporated into the protein, polypeptide or label prior to reaction with the drug thiol but the drug thiol can also be reacted with the thiol reactive compound prior to reaction with the protein, polypeptide or label. Also, bis-maleimide compounds of varying length can be reacted with thiol containing proteins, polypeptides or labels for covalent coupling of the methadone derivatives. Conversely, the bis-maleimide compound can be reacted with the thiol derivative and subsequently to the thiol containing protein, polypeptide or label.

Common bis-maleimides are bis-maleimidohexane from Pierce, N,N'-bis(3maleimidopropionyl)-2-hydroxy-1,3-propanediamine from Sigma Chemical Co., St. Louis, Mo., and 1,1'-(methylenedi-4,1-phenylene)-bismaleimide from Aldrich Chem. Co., Milwaukee, Wis. The thiol methadone derivatives can also form disulfides with thiol containing polypeptide, protein or label molecules as a means to incorporate the derivative into the molecule.

The use of drug derivatives, immunogens and protein and polypeptide conjugates for generating antibodies and for use in the immunoassay process is described, for example, in U.S. Pat. Nos. 4,067,774, 4,952,336, 5,028,535 and 5,089,391.

EXPERIMENTAL EXAMPLES

Example 1

Preparation of 2,2-Diphenyl-4-dimethylaminopentanenitrile

Sodium hydride (19.5 g of an 80% dispersion in oil, 0.65 mol) was added to a 1 L 3-neck round bottom flask and triturated twice with hexane (150 mL) to remove the oil). Tetrahydrofuran (THF)(150 mL) was added to the flask followed by a stir bar and the resulting suspension stirred under argon whilst adding a solution of diphenylacetonitrile (58 g, 0.3 mol) in THF (150 mL) dropwise via a dropping funnel over 40 minutes. It became necessary to cool the flask in a cold water bath during the addition due to the exotherm generated. After stirring a further 10 minutes at room temperature the flask was fitted with a reflux condenser and placed in an ice bath. The resulting green suspension was then treated with 2-dimethylaminoisopropyl chloride hydrochloride (54 g, 0.34 mol) portionwise, via an addition funnel, over 15 minutes with stirring.

The yellow mixture was refluxed on a heating mantle for 5 hours, during which time it became thick and then thinned out. After cooling, the THF was evaporated, the residual yellow solid treated with water (150 mL) and extracted with ether (2×150 mL). The extract was washed with water (3×100 mL) and dried over anhydrous magnesium sulfate. After evaporation of the ether, the thick oily orange residue was treated with ice-cold hexane to afford a white solid. The contents were stirred in an ice/water bath for 30 minutes and the solid collected by filtration washing with ice-cold hexane. After drying in a vacuum desiccator there was obtained 44.9 g (54%) white solid m.p. 88°–89° C.

This product was used without further purification in the next step.

Example 2

Preparation of 7,7-Diphenyl-6-keto-9-dimethylaminodecanoic acid hydrochloride

This compound was prepared according to a literature procedure (U.S. Pat. No. 3,843,696) starting with 2,2-Diphenyl 4-dimethylaminopentanenitrile (10 g) from the previous step to afford 8.5 g product.

Example 3

Preparation of 1-N-(2-Butyrothiolactone) amido-6,6-diphenyl-5-keto-8-dimethylaminononanane To a stirred suspension of homocysteine thiolactone hydrochloride (1.84 g, 11.96 mmol) in dry DMF (100 mL) there was added pyridine (3 mL, 37.08 mmol). After 10 minutes, when complete solution was effected, a solution of 7,7-diphenyl-6-keto-9-dimethylaminodecanoic acid hydrochloride (5 g, 11.96 m mol) in dry DMF (20 mL) was added followed by 1-(3-dimethylaminopropyl)-3-ethylcarbodiimide hydrochloride (2.52 g, 13.16 mmol). The yellow solution was stirred under argon for 5 hours. The DMF was evaporated, the residual oil treated with water (100 mL) and extracted with methylene chloride (3×50 mL). The extract was evaporated to an amber colored oil which was treated with 0.5M potassium phosphate/0.1M potassium borate Ph 7 buffer (100 mL) and extracted with ethyl acetate (3×50 mL). The extract was dried over anhydrous magnesium sulfate, filtered and evaporated. The gummy residue was treated with ether (100 mL), decolorizing charcoal was added and the mixture filtered through celite. The light yellow filtrate was acidified to Ph 1–2 by dropwise addition of a 1M solution of hydrogen chloride in ether (10 mL) with stirring. The resulting cream colored solid which precipitated was collected by filtration washing with ether (50 mL). After drying in a vacuum desiccator there was obtained 4.1 g cream colored, hygroscopic solid which was 85% pure by HPLC.

A small portion of this product (60 mg) was purified using a C18 reverse phase semi-preparative HPLC column and eluting with 20 mM potassium phosphate Ph 4.6/methanol (0–100% over 50 minutes). The product fraction eluting at 34–37 minutes was evaporated.

The residue was treated with methylene chloride (5 mL) and filtered from insoluble buffer salts. The filtrate was evaporated to afford, after vacuum drying, 35 mg of 1-N-(2-Butyrothiolactone)amido-6,6-diphenyl-5-keto-8-dimethylaminononane phosphate salt as a white hygroscopic solid. This product is now 100% pure by HPLC.

NMR (DMSO d-6) δ8.08 (m, 1H), δ7.32 (m, 10H), δ2.29 (s, 6H), δ1.20 (m, 4H), δ0.43 (d, 3H).

Example 4

Preparation of 1-N-(Cysteine) amido-6-6-diphenyl-5-keto-8-dimethylaminononane

1-N-(2-Butrlothiolactone)amido-6,6-diphenyl-5-keto-8-dimethylaminononane(1.0 mg, 1.6 μmol) was dissolved in 70/30, v/v dimethylformamide/water (65 μL). 1N potassium hydroxide solution (16 μL) was added and the solution allowed to stand at room temperature for 3 minutes. 0.5M potassium phosphate/0.1M potassium borate pH 7 buffer (which was then made 1N in hydrochloric acid) was immediately added in 5 μL increments until pH 7 was attained.

The title compound in solution was used as is to react with thiol reactive groups, such as maleimides, alkyl halides or thiols which are either free in solution or are coupled to proteins, polypeptides or labels.

I claim:
1. Compounds of the formula:

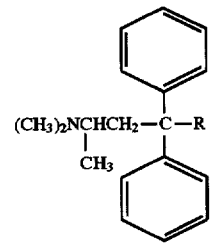

where R is a linking group selected from the group consisting of:

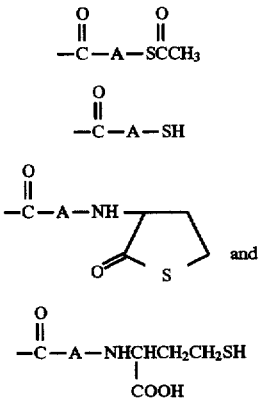

where A is a linking group of from 1 to 20 carbons and from 0 to 10 heteroatoms, either branched or straight chain, wherein said heteroatoms are selected from the group consisting of NH, O and S.

2. A compound of the formula:

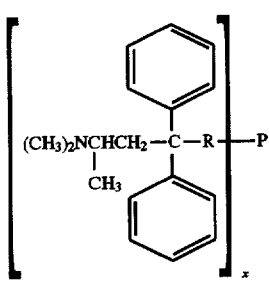

where P is an antigenic protein or polypeptide or a protein, polypeptide or label;
where x is at least one and not greater than 100;
where R is a linking group selected from the group consisting of:

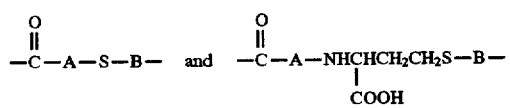

where A is a linking group of from 1 to 20 carbons and 0 to 10 heteroatoms either branched or straight chain, wherein said heteroatoms are selected from the group consisting of NH, O and S;
where B is a linking group attached to a protein, polypeptide or label, wherein B is selected from the group consisting of;

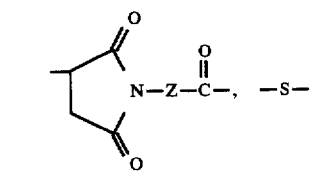

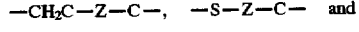

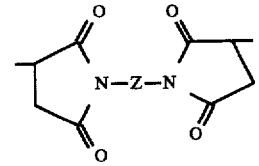

where Z is a linking group of from 1 to 20 carbons and 0 to 10 heteroatoms and may be branched or straight chain, wherein said heteroatoms are selected from the group consisting of NH, O and S.

3. An antibody or fragment thereof that specifically binds to the compound of claim 2.

4. Compounds of formula:

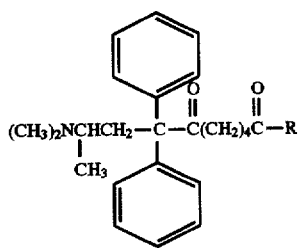

Where R is a linking group selected from the group consisting of:

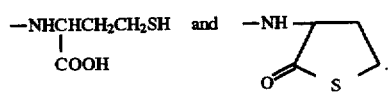

5. A compound of the formula:

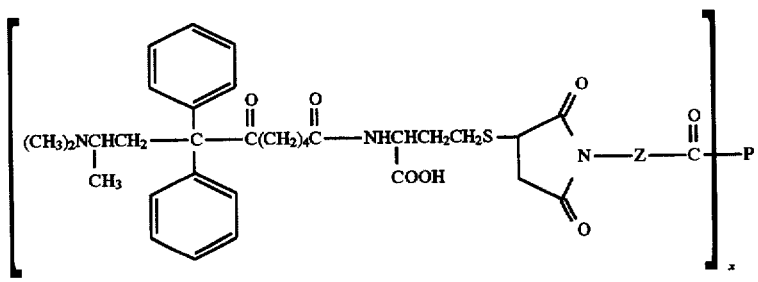

where P is an antigenic protein or polypeptide or a protein, polypeptide or label;

where x is at least one and not greater than 100;

where Z is a linking group of from 1 to 20 carbons and 0 to 10 heteroatoms and may be branched or straight chain, wherein said heteroatoms are selected from the group consisting of NH, O and S.

6. An antibody or fragment thereof that specifically binds to the compound of claim 5.

* * * * *